United States Patent [19]

Tepic

[11] Patent Number: 5,223,429
[45] Date of Patent: Jun. 29, 1993

[54] METHOD FOR THE MASS GROWTH OF CELLS IN A THIN FILM OF NUTRIENT MEDIUM FOAM

[76] Inventor: Slobodan Tepic, Oberstrasse 55, Davos-Platz, Switzerland, CH-7270

[21] Appl. No.: 611,470

[22] Filed: Nov. 9, 1990

Related U.S. Application Data

[63] Continuation of Ser. No. 384,103, Jul. 21, 1989, abandoned, which is a continuation of Ser. No. 900,173, Jun. 16, 1986, abandoned.

[51] Int. Cl.$^5$ .............. C12N 5/00; C12N 5/02; C12N 9/99; A23L 1/202
[52] U.S. Cl. .............. 435/240.3; 435/240.2; 435/240.23; 435/240.24; 435/285; 435/286; 435/287; 435/313; 435/812
[58] Field of Search ............ 435/240.2, 240.3, 240.23, 435/240.24, 284, 285, 286, 287, 812, 313, 315

[56] References Cited

U.S. PATENT DOCUMENTS

| | | | |
|---|---|---|---|
| 3,717,551 | 2/1973 | Bizzini et al. | 435/240.24 |
| 3,948,725 | 4/1976 | Irie | 435/240.3 |
| 4,144,126 | 3/1979 | Burbidge | 435/240.24 |
| 4,224,413 | 9/1980 | Burbidge | 435/284 |

OTHER PUBLICATIONS

Large Scale Cell Culture Technology (1987) Edited by Bjorn K. Lydersen, pp. 69-70, Macmillan (U.S.A.) and Collier Macmillan (Canada) Publishing Company.

*Primary Examiner*—Robert J. Hill, Jr.
*Assistant Examiner*—Gian P. Wang
*Attorney, Agent, or Firm*—Walter C. Farley

[57] ABSTRACT

A method for the mass growth of cells (2) which consists in growing the cells (2) in a thin film, e.g. a bubble or foam, of nutrient medium (4), which is continuously recirculated to the bulk medium (1) for replenishing. Growth rate and yields obtained with this method in large scale cell culturing are far superior to those obtained by know methods, due to the increased metabolic exchange of the cells (2) with the environment.

8 Claims, 5 Drawing Sheets

METHOD FOR THE MASS GROWTH OF CELLS IN A THIN FILM OF NUTRIENT MEDIUM FOAM

CROSS REFERENCE TO RELATED APPLICATION

This is a continuation of Ser. No. 384,103 filed Jul. 21, 1989, now abandoned, which was a continuation of Ser. No. 900,173 filed Jun. 16, 1986, now abandoned.

This invention relates to a method for the mass growth of cells and an apparatus for the carrying out thereof.

In vitro cell growth is required for many purposes, for instance for the production of vaccines and cell products, for human use and for research purposes. In in vitro cultures most cells will not divide unless they attach to a solid surface and spread out. This requirement is commonly referred to as "anchorage" requirement. Cells growing on such cell-receptive surfaces adhere firmly to it and form a closed, dense, cell layer (monolayer). The principle of the growth of cells on the surface of a substance therefore establishes a natural limit for production due to the limited size of surface available for culture. For several years it has been attempted to find a practical solution for this limitation by enlarging artificially the surface available for the cell growth, as disclosed for example in the British Patent Specification No. 1,525,022.

It can be stated that none of these known systems for the mass growth of cells has reached the stage of routine operational production of cells or of cell products. From a practical standpoint, a true mass growth of cells has not been obtained with any system, and from a theoretical standpoint all the systems have serious disadvantages, for instance the possibility of microbic and cellular contamination, and the difficulty of rationalization and automatization. The invention as claimed is intended to provide a remedy. It solves the problem how to produce a true mass growth of cells without the need of a solid surface and more particularly how to design an apparatus for carrying out this process in an industrial manner with the possibility of automatization and rationalization of the process.

It has surprisingly been found that the crucial effect of "anchoring" is the change in shape of the cell, i.e. the spreading out, rather than the cell's physical contact with a solid surface. Provided that all other conditions for growth (suitable growth medium, temperature, oxygen etc.) are satisfied a flattened-out cell will divide no matter how the flattening was effected.

The method practiced with the present invention allows for spreading out cells within thin films formed by the growth medium itself. In addition to fulfilling the basic requirements of cells flattening, the method offers superior conditions for metabolic exchange with the environment, resulting in higher growth rates, and hence higher yields in large scale cell culturing. The method is particularly well suited for continous growing of cells for the ease of monitoring and control. The present invention, therefore, has far reaching implications in the field of large scale cell growing.

In the preferred embodiment of the invention cells are grown in the walls of bubbles formed from the growth medium containing cells, much like the familiar soap bubbles, preferably by a continuous bubble production process. Addition of foetal calf serum, which is still required for most cell lines makes the growth medium suitable for bubble making. The nutrient medium in the bubbles is replenished simply by adding fresh medium in the bubble circulation path. Cell population is kept at optimum by a cell removal rate equal to the growth rate. Life time of the bubble can be much longer than the recirculation time. Recirculation of the bubble should not allow a cell to round up once it was spread out during "bubble time". The amount of medium at disposal of each cell in the bubble wall is small, but replenishment at resuspension in the bubble circulation process is sufficient for the next bubble cycle. In contrast to anchored cells, all of the cell's surface is available for metabolic exchanges. Oxygen and carbon-dioxide exchanges in particular, are far superior to those obtainable in suspension (with micro-sphere anchorage) cultures.

These and other objects and advantages of the invention will become apparent from the following detailed description taken in conjunction with the accompanying drawings wherein.

Figure 1A:
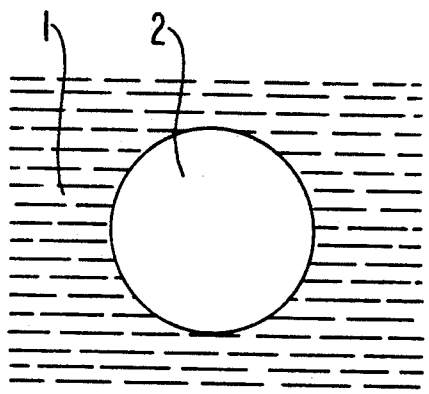
FIG. 1a shows a cell (2) floating freely in bulk medium (1). When in suspension the cell (2) is more or less spherical in shape.
Figure 1B:
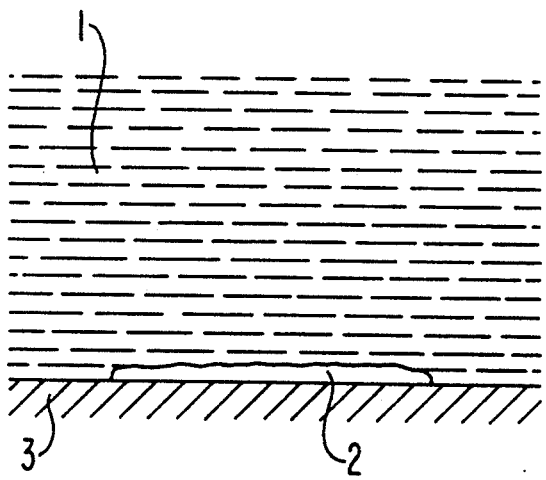
FIG. 1b shows a cell (2) which is anchored to a suitable solid surface (3). In this anchored state the cell (2) is spread out by attractive forces acting between the cell (2) and the solid surface (3).
Figure 1C:
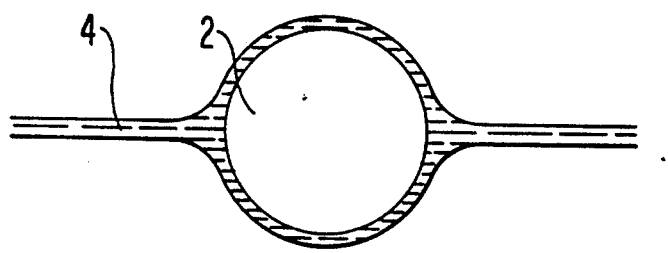
FIG. 1c shows a cell (2) trapped within a thin film of medium (4).
Figure 1D:
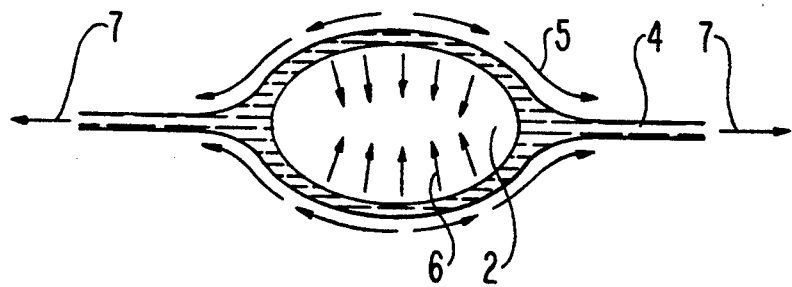
FIG. 1 (a to e) illustrates the basic principle of the invention by means of sections through cells of different wall shape.
Figure 1E:
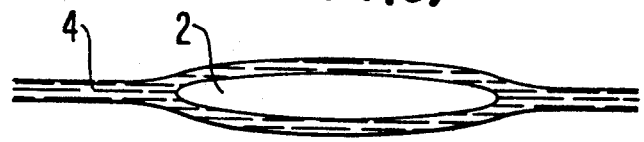

Placed in this thin film (4) from the bulk medium (1) the cell (2) is initially spherical in shape. FIGS. 1d and e show how surface tension forces (5) tend to minimize the protrusion caused by the cell leading to a flattened cell (2). The degree of flattening depends on the equilibrium "stiffness" of the cell (2) and the magnitude of the resultant "squeeze" stresses (6) induced by film tension (7). The dynamics of the spreading out of the cells (2) depends on the ratio between viscous and elastic components of cell resistance to shape distortion. Usually the elastic component of resistance (stiffness) is very small, and very weak stresses, given enough time, will spread out the cell and trigger its division cycle.

Figure 2:
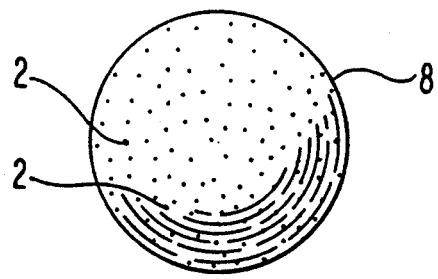
FIG. 2 shows a perspective view of a bubble of nutrient medium containing cells.

Various spatial organisations of the cell growth film are possible. The film may depend on a solid support or be self supporting. FIG. 2 shows the simplest form that unsupported films may take—that of a sphere or "bubble" (8). A colony of cells is grown in a multitude of such bubbles, maintained, as described below, in a chamber of controlled environment.

Figure 3:
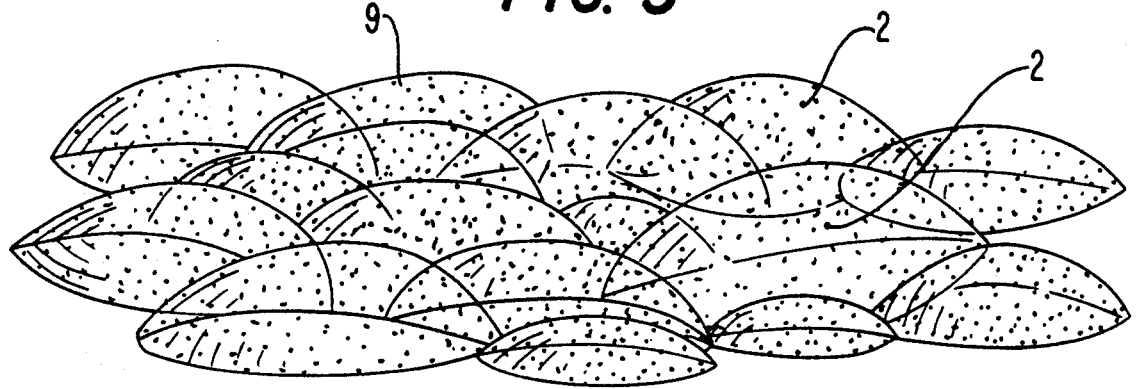
FIG. 3 illustrates a perspective view of a foam of nutrient medium containing cells.

FIG. 3 shows an interconnected, self-supporting film in the form of a foam (9). As in the case of bubbles, the foam is maintained in a specially designed growth chamber.

Figure 4:
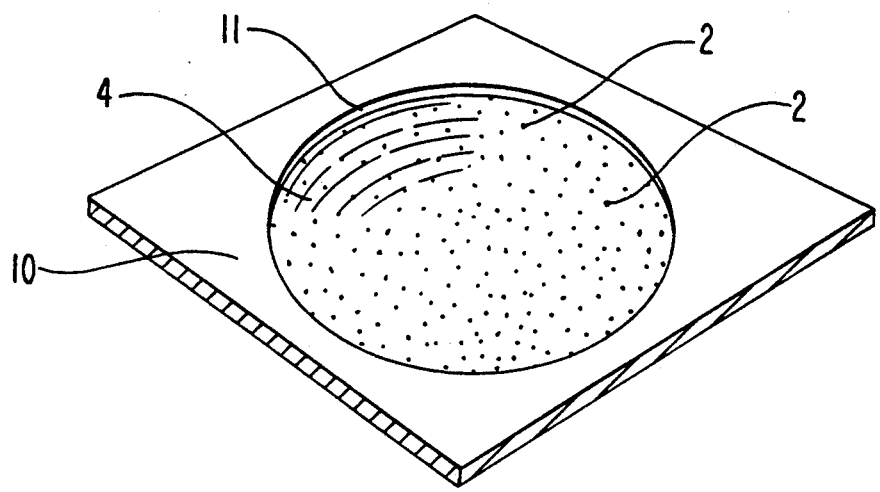
FIG. 4 is a perspective view of a solid frame supporting a thin film of nutrient medium.

FIG. 4 shows a solid frame which supports thin growth films (4) over a multitude of perforations (11). A similar effect can be achieved by frames constructed of nets.

Additions of foetal calf serum (still required for most cell lines) makes the growth medium suitable for film formation. If necessary, film stability may be improved by suitable additives as disclosed in the British Patent Specification No. 1,525,022.

Figure 5:
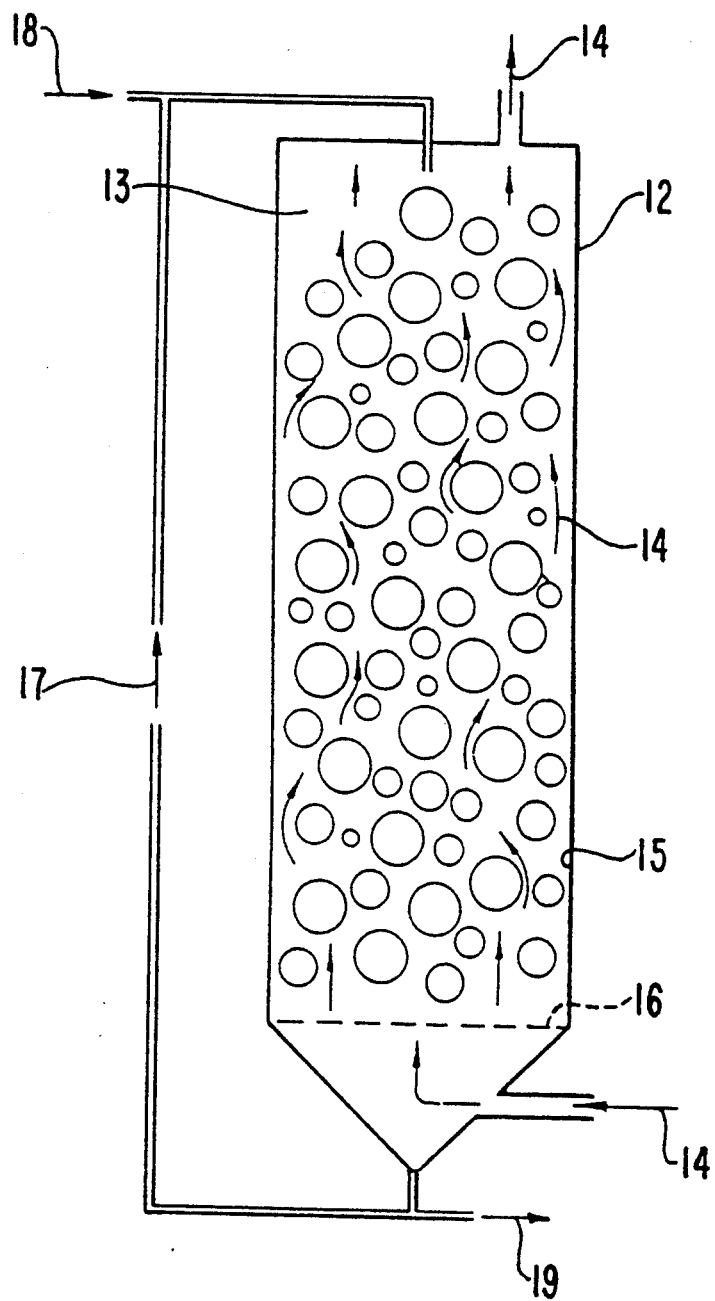
FIG. 5 is a schematic representation of a growth chamber for producing and maintaining of bubble cell colonies.

FIG. 5 shows the basic features of a growth chamber (12) for maintenance of bubble cell colonies. Bubbles are formed from the cell-containing medium in the upper section (13) of the chamber (12) and are slowly descending against a stream (14) of 100% humid air of regulated temperature and composition. Each bubble carries an electrical charge (excess of a particular ion imposed at bubble formation) sufficient to keep them apart as they descend. The vertical walls (15) of the chamber (12) are also charged electrically. Furthermore the control of descent of the bubbles can also be effected or supplemented by an appropriate electrical field. Once the bubbles reach the bottom (16), they burst and the medium with the cells is circulated back (as represented by arrow (17)) to the top of the chamber (12) and into new bubbles. The medium is continuously replenished, as represented by arrow (18). Cell population is kept at optimum by cell removal, as represented by arrow (19), at a rate equal to the growth rate. Descent or "bubble time" must be longer than recirculation time, so that recirculation does not allow a cell to round up once it was spread out during "bubble time".

Figure 6:
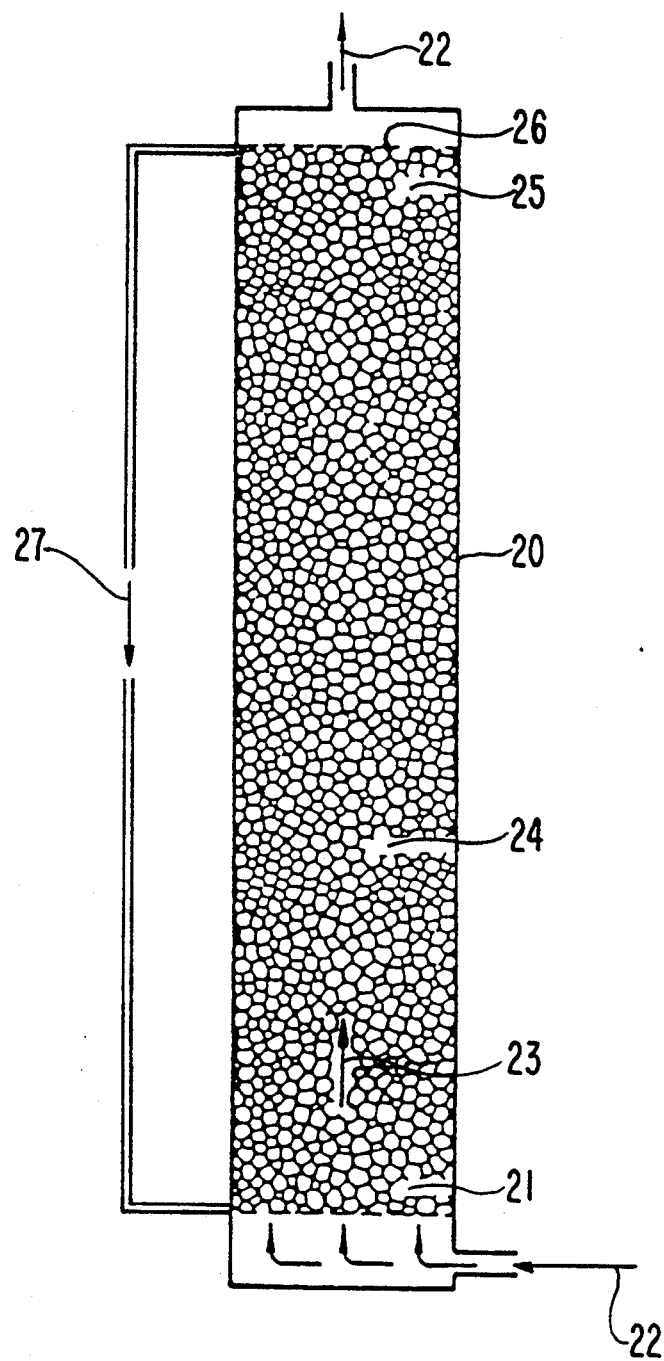
FIG. 6 shows a schematic view of a chamber for cell incubation in foam films.

FIG. 6 shows a chamber (20) for cell incubation in films of foam. The foam is continuously formed at the bottom (21) of the chamber (20) by a flow of air (22) of controlled composition, temperature and 100% humidity in order to avoid evaporation of the medium. The foam ascends as represented by arrow (23) within the chamber (20) at the rate determined by the air flow intensity. This should be very low to keep the foam structure (24) as stable as possible. At the top of the chamber (25) the foam breaks or is broken against a suitable barrier (26) and the medium with the cells is circulated back, as represented by arrow (27) to the bottom of the chamber (21) and reconverted into foam. Again the "foam time" should be much longer than the time needed for recirculation to avoid cell rounding. The efficiency of space utilisation in this particular configuration of growth film is much higher than in the case of bubble colonies.

Figure 7:
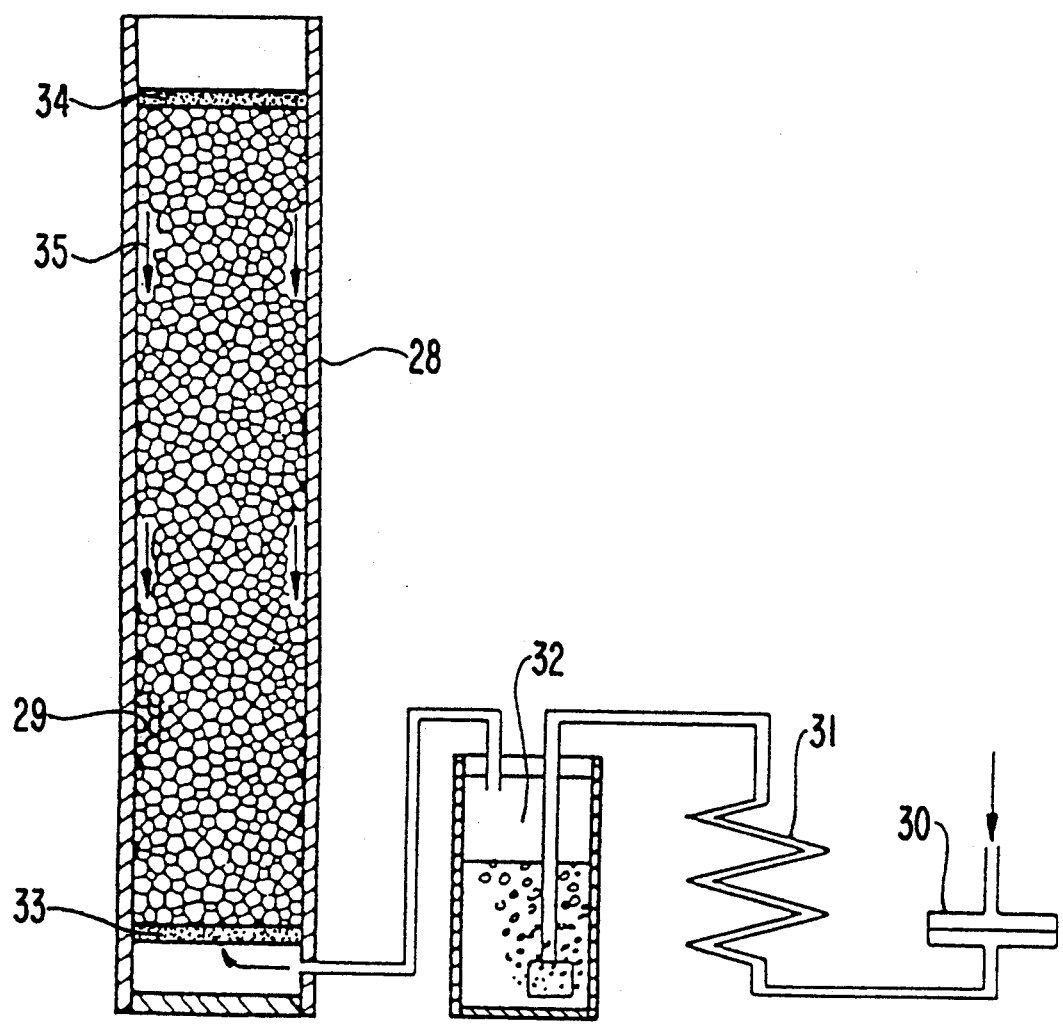
FIG. 7 is a schematic view of a laboratory scale apparatus for cell incubation in foam films.

FIG. 7 shows a laboratory scale apparatus consisting of a simple glass tube (28). All solid surfaces contacted by the medium are siliconized (29) in order to avoid cell anchorage. Air with an increased content of carbon dioxide for pH control is sterilized by filtration (30), heated up to the incubation temperature (31), saturated with moisture (32) and then introduced through a teflon filter (33) at the bottom of the chamber.

The hydrophobic teflon filter (33) prevents the growth medium with cells from running out. The foam is formed from any medium collected on top of the filter and slowly pushed upwards. A foam breaker (34) consisting of a teflon filtered at the top of the tube allows air to escape while the medium runs down the walls, as represented by arrow (35) to the bottom of the tube where it is reconverted into foam.

I claim:

1. A method for the mass growth of cells, wherein the cells are not supported on a solid support and wherein said cells are grown in a thin film of nutrient medium, said method comprising the steps of
   establishing a thin film of nutrient medium, and
   growing cells in the thin film, wherein said cells are not supported on a solid support.

2. A method according to claim 1, wherein the thin film consists of the wall of a bubble (8).

3. A method according to claim 1, wherein the thin film consists of the walls of a foam (9).

4. A method according to claim 3 wherein the cells (2) are subjected to a recirculation process in which the cells (2) in the thin film of nutrient medium (4) are recirculated in the form of bulk medium (1) for replenishing and then placed again in a thin film of nutrient medium (4).

5. A method according to claim 4, wherein the recirculation process is continuous.

6. A method for the mass growth of cells, wherein the cells are not supported on a solid support and wherein said cells are grown in a thin film of nutrient medium, said method comprising the steps of
   establishing a substantially self-supporting structure of thin film of nutrient medium,
   placing a plurality of cells within said thin film structure,
   maintaining said thin film structure under conditions conducive to cell growth for a sufficient time to grow cells within the thin film.

7. A method according to claim 6 and further including
   providing a chamber for containing the thin film structure, and
   slowly moving the thin film structure carrying the cells through the chamber while maintaining the conditions conducive to cell growth within the chamber.

8. A method according to claim 7 wherein the thin film structure comprises a mass of bubbles.

* * * * *